(12) United States Patent
Dontas

(10) Patent No.: US 8,563,798 B2
(45) Date of Patent: Oct. 22, 2013

(54) ENCLOSING BANDAGE FOR PROVIDING COMFORTABLE WOUND CARE AND LIMITING FLUID LEAKAGE

(76) Inventor: Kalliope Dontas, Yonkers, NY (US)

(*) Notice: Subject to any disclaimer, the term of this patent is extended or adjusted under 35 U.S.C. 154(b) by 265 days.

(21) Appl. No.: 12/717,191

(22) Filed: Mar. 4, 2010

(65) Prior Publication Data
US 2011/0218509 A1 Sep. 8, 2011

(51) Int. Cl.
*A61F 13/00* (2006.01)
*A61F 13/15* (2006.01)

(52) U.S. Cl.
USPC ............... 602/43; 602/41; 602/42; 602/44; 602/58; 602/67; 604/385.01; 604/385.23; 604/385.24; 604/385.25

(58) Field of Classification Search
USPC ............ 602/3, 41–44, 60–65, 67, 58, 68, 79; 128/888, 889, 891, 892; 604/385.01, 604/385.09, 385.23–385.25, 385.201
See application file for complete search history.

(56) References Cited

U.S. PATENT DOCUMENTS

| | | |
|---|---|---|
| 3,486,501 A | 12/1969 | Erickson et al. |
| 3,521,632 A | 7/1970 | Graham |
| 3,528,417 A | 9/1970 | Gardner et al. |
| 3,713,450 A | 1/1973 | Williams |
| 3,798,678 A | 3/1974 | Pierron et al. |
| 3,934,583 A | 1/1976 | Hollingshead et al. |
| 4,027,667 A | 6/1977 | Swallow et al. |
| 4,187,855 A | 2/1980 | Paulus et al. |
| 4,368,547 A | 1/1983 | dePolo |
| 4,590,932 A | 5/1986 | Wilkerson |
| 4,811,727 A | 3/1989 | Etienne |
| 4,820,296 A | 4/1989 | Masliyah |
| 5,005,567 A | 4/1991 | Gilman et al. |

(Continued)

FOREIGN PATENT DOCUMENTS

| | | |
|---|---|---|
| FR | 2924329 A1 | 5/2009 |
| JP | 2005042240 A | 2/2005 |

(Continued)

OTHER PUBLICATIONS http://www.lympha-press.com/uploads/files/newsletters/1102007082019.htm Downloaded on Jul. 20, 2009 The ComfySleeve is the newest garment for use with Lympha Press Mini 201M or Lympha Press Plus 1033.

(Continued)

*Primary Examiner* — Kim M Lewis
(74) *Attorney, Agent, or Firm* — Tracy Jong Law Firm; Tracy P. Jong; Cheng Ning Jong

(57) ABSTRACT

A bandage for improved wound care is disclosed. The bandage comprises a non-adherent, deformable inner layer, a leak-proof outer layer that is substantially coextensive with the inner layer, and an absorbent middle layer contacting both the inner and outer layers. An adhesive strip and adhesive tabs along the bandage's side attach and adjust the fit of the bandage to securely hold the absorbent layer in contact with the wound, without any adhesive touching the skin, thereby eliminating pain and discomfort upon removal or replacement. The bandage allows substantial freedom of motion without slipping. The adhesive strip and tabs secure the bandage in place without any adhesive touching the skin, thereby providing convenience and causing no pain or discomfort upon removal or replacement of the bandage. The bandage may use a non-stick netting material layer to improve patient comfort, and elastic cuffs to improve fit and leakage.

1 Claim, 3 Drawing Sheets

(56) References Cited

U.S. PATENT DOCUMENTS

| | | | |
|---|---|---|---|
| 5,054,129 A | 10/1991 | Baehr | |
| 5,135,473 A | 8/1992 | Epler et al. | |
| 5,425,702 A | 6/1995 | Carn et al. | |
| 5,522,794 A | 6/1996 | Ewall | |
| 5,538,502 A | 7/1996 | Johnstone | |
| 5,682,617 A | 11/1997 | Tumas | |
| 5,779,657 A | 7/1998 | Daneshvar | |
| 5,806,096 A | 9/1998 | Pennington | |
| 5,823,977 A * | 10/1998 | Dalyea ............................. | 602/3 |
| 5,960,795 A | 10/1999 | Schultz | |
| 5,968,002 A | 10/1999 | Morrisseau | |
| 5,994,612 A | 11/1999 | Watkins | |
| 6,055,668 A | 5/2000 | Gros et al. | |
| 6,063,049 A | 5/2000 | Watkins | |
| 6,152,137 A | 11/2000 | Schwartz et al. | |
| 6,234,117 B1 | 5/2001 | Spatt | |
| 6,390,885 B1 | 5/2002 | Brooks | |
| 6,548,728 B1 | 4/2003 | Faries, Jr. et al. | |
| 6,715,158 B1 | 4/2004 | Hay | |
| 6,748,601 B2 | 6/2004 | LaShoto et al. | |
| 6,843,786 B1 | 1/2005 | Thuren et al. | |
| 6,892,734 B1 | 5/2005 | Schleicher et al. | |
| 6,927,316 B1 | 8/2005 | Faries, Jr. et al. | |
| 6,982,358 B1 | 1/2006 | Barker | |
| 7,000,616 B2 | 2/2006 | Diaz et al. | |
| 7,003,804 B2 | 2/2006 | Lewis | |
| 7,047,572 B2 * | 5/2006 | Hopkins ............................. | 2/400 |
| D546,003 S | 7/2007 | Choi et al. | |
| 7,418,741 B2 | 9/2008 | Rogers | |
| 7,485,111 B1 | 2/2009 | Choi et al. | |
| 7,563,941 B2 | 7/2009 | Lebner et al. | |
| 2003/0167548 A1 | 9/2003 | LaShoto et al. | |
| 2004/0006806 A1 | 1/2004 | Gabriel | |
| 2004/0030270 A1 | 2/2004 | Johnson | |
| 2004/0127828 A1 * | 7/2004 | Masini ............................. | 602/41 |
| 2006/0084902 A1 | 4/2006 | Schleicher et al. | |
| 2007/0042025 A1 | 2/2007 | Gladman et al. | |
| 2007/0777860 | 4/2007 | Brooks | |
| 2007/0167884 A1 | 7/2007 | Mangrum et al. | |
| 2007/0214552 A1 | 9/2007 | Ferber | |
| 2008/0083055 A1 | 4/2008 | Onda | |
| 2008/0269654 A1 | 10/2008 | Chardon-Bras et al. | |
| 2009/0171259 A1 | 7/2009 | Soerensen et al. | |

FOREIGN PATENT DOCUMENTS

| | | |
|---|---|---|
| JP | 2007297742 A2 | 11/2007 |
| JP | 2009050299 A2 | 3/2009 |
| WO | 9503018 A1 | 2/1995 |
| WO | 0006068 A2 | 2/2000 |
| WO | 0024349 A1 | 5/2000 |
| WO | 0044327 A1 | 8/2000 |
| WO | 2007003900 A2 | 1/2007 |
| WO | 2007036751 A2 | 4/2007 |

OTHER PUBLICATIONS http://www.aetna.com/cpb/medical/data/1_99/0062.html Downloaded on Jul. 20, 2009, Burn Garmets.
http://www.medicalsupplygroup.com/CORE_WOUND_CARE/TUBULAR_GAUZE_RETAINERS/BAL81320/product.aspx Downloaded on Jul. 20, 2009, Orthopedic Stockinette.
http://www.healingenhancements.com/browseproducts/Surgical-Vest-(37023).HTML Downloaded on Jul. 20, 2009.

* cited by examiner

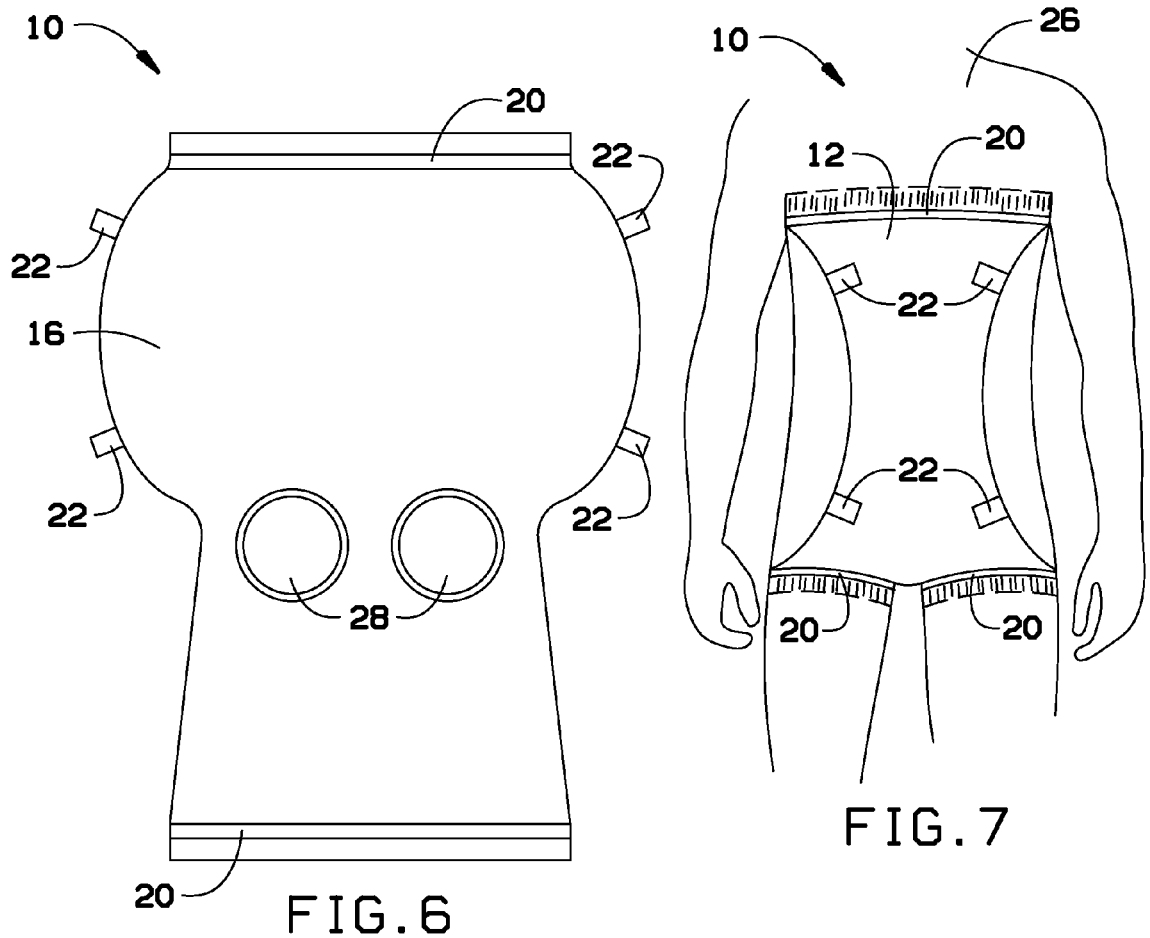
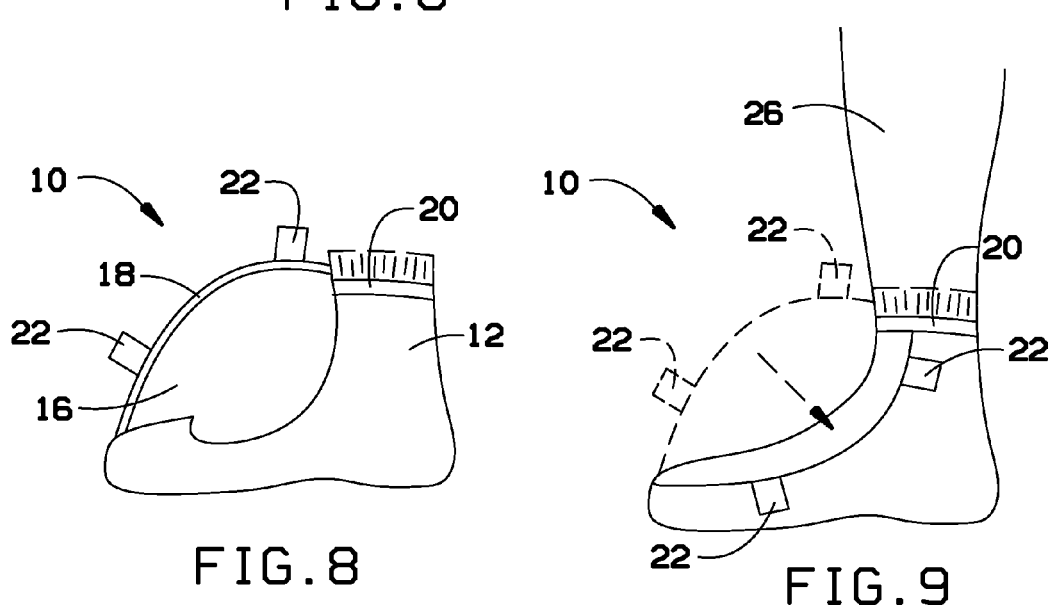

ENCLOSING BANDAGE FOR PROVIDING COMFORTABLE WOUND CARE AND LIMITING FLUID LEAKAGE

FIELD

This application relates generally to wound bandages and garments, and more specifically to a wound care bandage or garment that covers specific portions of a patient's body such as an arm, a leg, a foot, or an abdominal region.

BACKGROUND

The dressing, changing, and care of wounds may require the placement and securing of absorbent bandages covering the wound. This is true whether the wound or wounds are from a surgery, a sharp blade, a projectile, a burn, a blunt impact, an illness, infection, stitches, transplant, or other reason for covering the surface of a patient's body with a bandage. Currently, many surgeries are performed with lasers and/or robotics which require several small punctures instead of traditional surgery using larger incisions. These smaller punctures are usually farther apart than what can be accommodated by a single traditional bandage, and therefore require more than one traditional bandage which creates an added inconvenience. Known bandages require time, skill and precision for proper application, which if not properly applied, may result in slippage or leaking of excess fluids, or may even result in uncovering the wound or wounds when the patient moves. Known bandages can also result in discomfort when adhesive is both applied to and then removed from the patient's skin.

SUMMARY

A bandage used for improved wound care is claimed, including a non-adherent, deformable inner layer, a leak-proof outer layer that is substantially coextensive with the inner layer, and an absorbent middle layer contacting both the inner and outer layers. An adhesive strip and two or more adhesive tabs along one side serve to attach and adjust the fit of the bandage to securely hold the absorbent layer in contact with the wound and allow substantial freedom of motion without slipping. The adhesive strip and tabs secure the bandage in place without any adhesive touching the skin, thereby providing convenience and causing no pain or discomfort upon removal or replacement of the bandage. Elastic cuffs on the top and bottom sides prevent excess fluids from leaking and help hold it in place. One embodiment includes elastic around leg holes.

The bandage or garment may be designed to wrap around a part of a body having a wound. The bandage may use a non-stick netting material layer to improve patient comfort, and elastic cuffs to improve fit and leakage. The fitted garment may appear similar to a sleeve having a tube shape, and may cover large areas to reduce the probability of the bandage slipping off of the wound area.

In one embodiment, the bandage comprises: an inner layer, a middle layer, an outer layer, a top edge, a bottom edge, a right edge and a left edge, the inner layer being deformable and non-adherent, the outer layer being substantially impermeable to liquid, and being substantially coextensive with the inner layer, the middle layer being disposed between and contacting both the inner and outer layers, the middle layer being absorbent; at least one attachment strip connected to the inner and/or outer layers along substantially the entire length of the right edge and/or the left edge; at least one adjustable tab connected to the right edge and/or the left edge; and at least one cuff connected to the outer layer and disposed at a selected distance from the top edge and/or the bottom edge.

In some embodiments, the inner layer includes a woven material. In other embodiments, the inner layer includes a netting material. In other embodiments, the inner layer is attached along at least one edge to the outer layer by a netting edge seal. In other embodiments, the outer layer includes an elastic leak-proof material. In other embodiments, the middle layer is connected to the inner layer and/or the outer layer. In other embodiments, the middle layer adheres to the inner layer and/or the outer layer.

In some embodiments, the attachment strip includes an adhesive and/or a hook and loop system. In other embodiments, the adjustable tab includes an adhesive and/or a hook and loop system. In other embodiments, at least one cuff includes a band of elastic material having a selected width. In other embodiments, the inner layer is a flat rectangular sheet having a selected width and a selected length. In still other embodiments, the inner layer includes two substantially circular elastic holes having a diameter and location disposed to enable insertion of a human leg into each hole of the two substantially circular elastic holes. In other embodiments, the right edge and/or the left edge, includes a plurality of attachment points on the outer side for connection with the at least one attachment strip and/or the at least one tab.

In one embodiment, the bandage comprises: an inner layer, a middle layer, an outer layer, a top edge, a bottom edge, a right edge and a left edge, the inner layer being deformable and non-adherent, the outer layer being substantially impermeable to liquid, and being substantially coextensive with the inner layer, the middle layer being disposed between and contacting both the inner and outer layers, the middle layer being absorbent; an adhesive attached to least one of the inner layer and the outer layer, along substantially the entire length of the right edge and/or the left edge; at least one adhesive tab attached the inner layer and/or the outer layer, along substantially the entire length of the right edge and/or the left edge; and two elastic cuffs connected to the outer layer and disposed at a selected distance from the top edge and/or at the bottom edge. In some embodiments, the inner layer includes a woven material, a non stick material, and/or a netting material.

In some embodiments, the deformable material is attached along at least one edge to the outer side by a netting edge seal. In other embodiments, the middle layer comprises an elastic leak-proof material. In other embodiments, the middle layer is connected to at least one of the inner layer and the outer layer. In some embodiments, the middle layer adheres to the inner layer and/or the outer layer. In other embodiments, the inner side includes a flat rectangular sheet having a selected width and a selected length.

BRIEF DESCRIPTION OF THE DRAWINGS

FIG. 6 is a front view of an embodiment of the enclosing bandage to be used on a torso;

FIG. 7 is a front view of the embodiment of the enclosing bandage of FIG. 6 being used on a torso;

FIG. 8 is a side view of an embodiment of the enclosing bandage to be used on a foot; and FIG. 9 is a side view of the embodiment of the enclosing bandage of FIG. 8 being used on a foot.

DETAILED DESCRIPTION

Figure 1:
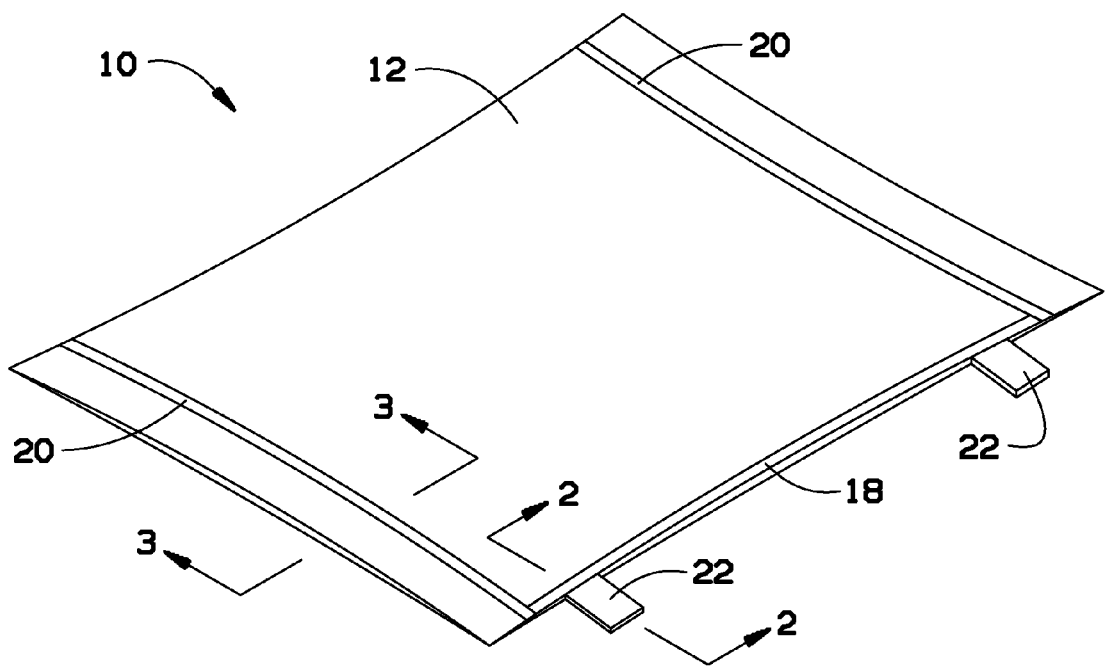
FIG. 1 depicts a perspective view of the enclosing bandage, according to various disclosed embodiments.

FIG. 1 depicts a perspective view of a general arrangement of the bandage. The illustrated bandage 10 is shown as being rectangular, but the invention is not so limited, and many different forms such as various quadrilaterals, ovals, triangles, non-plane shapes, and irregular shapes may be used without being beyond the present teaching. The bandage structure 10 includes an impermeable or leak proof layer 12, which will be the outer layer of the bandage. The bandage structure 10 may be wrapped around the wound in a tube like fashion with the leak proof layer 12 on the outside and adjustably attached and fitted by use of attachment strip 18 and adjustable tabs 22. The attachment strip 18 and adjustable tabs 22 may be formed using an adhesive, or hook and loop fasteners, or other attachment methods such as snaps, hooks, tape or combinations thereof. The garment may be adjusted to fit the specific patient and body portion by adjusting the connection location of the fasteners to provide a secure fit. In an embodiment the attachment strip 18 extends along substantially the entire side edge of the bandage 10.

Figure 2:
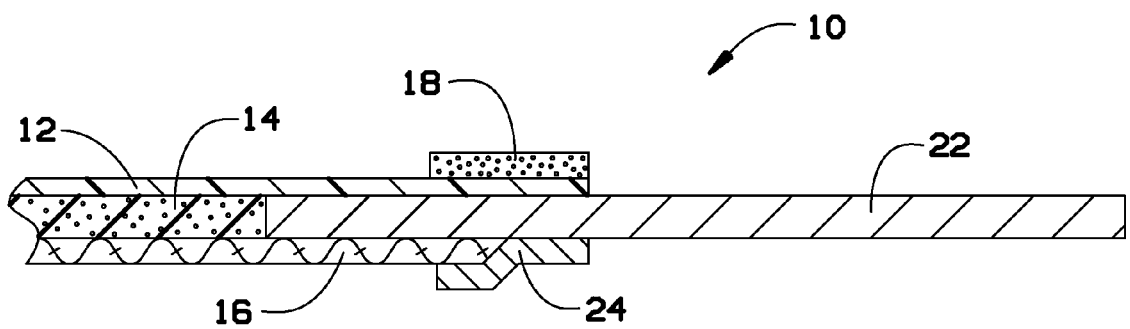
FIG. 2 illustrates a section view along line 2-2 of the embodiment of the enclosing bandage of FIG. 1.

FIG. 2 illustrates a section view along line 2-2 of the embodiment of FIG. 1 and includes a view of an absorbent middle layer 14, which may be attached over substantially the entirety of the surface of the leak proof outer layer 12. An inner layer 16 may also be attached to the absorbent layer 14 on the side opposite the outer layer 12, and may be formed of a non adherent or non stick material. The inner layer 16 in one embodiment may be formed of a woven, or netted material, and may be attached to the middle layer 14 across substantially the entire surface. The inner layer 16 may also be attached to the outer layer 12 by an edge seal 24, which may also help hold on the tabs 22.

Figure 3:
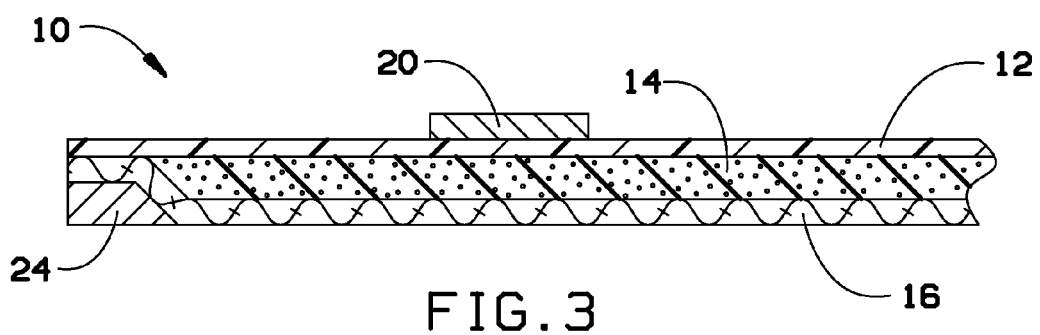
FIG. 3 illustrates a section view along line 3-3 of the embodiment of the enclosing bandage of FIG. 1.

FIG. 3 illustrates a section view along line 3-3 of the embodiment of FIG. 1 and includes either or both of a top and a bottom cuff 20, which may provide improved fit, secure hold, and reduced fluid leakage. The cuff 20 may be formed of an elastic material to provide secure leak sealing during movement.

Figure 4:
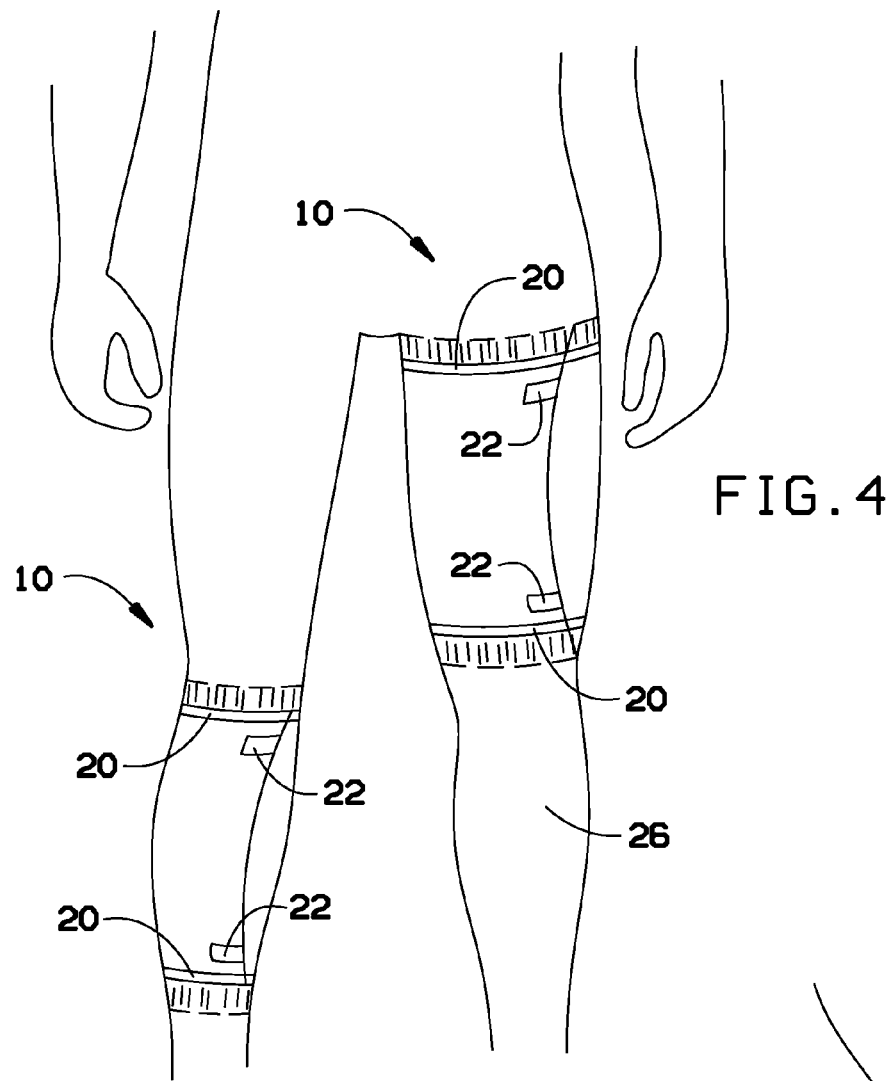
FIG. 4 illustrates a front view of an embodiment of the enclosing bandage used on a leg.

FIG. 4 illustrates a front view of an embodiment used on a leg and shows how the cuffs 20 help secure the bandage 10 to the thigh of patient body 26. The tabs 22, which may be an adhesive material, provide adjustable fit to the different leg diameters found on the upper thigh and the lower thigh, as well as the ability to use the same sized bandage on a large diameter thigh as well as on a lower diameter lower leg.

Figure 5:
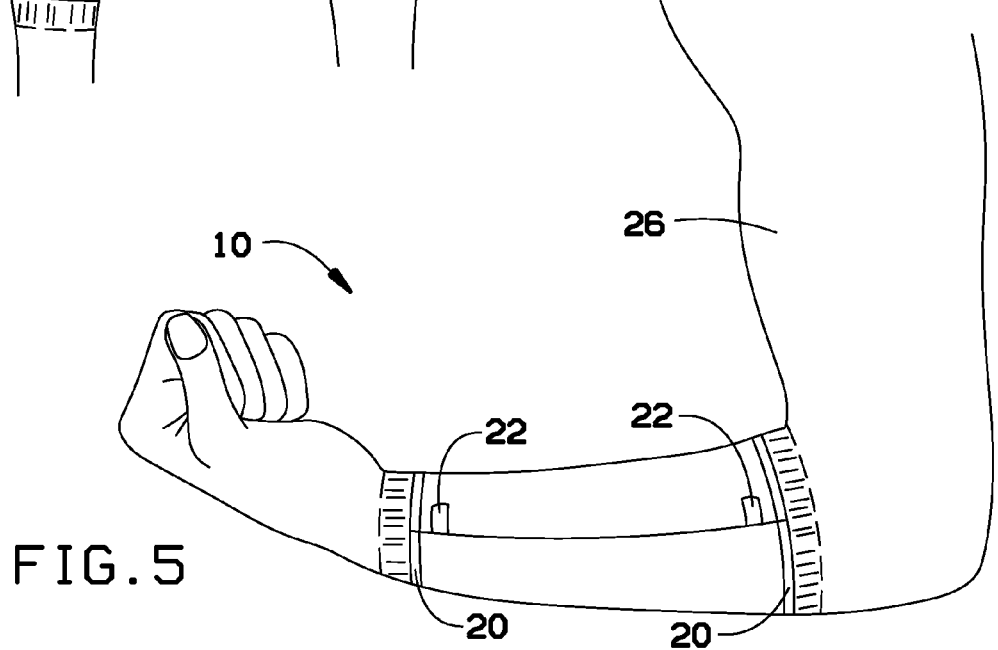
FIG. 5 is a side view of an embodiment of the enclosing bandage being used on an arm.

FIG. 5 is a side view of an embodiment used on an arm and shows how the combination of the side edge attachment strip and tabs 22 may adjust the fit on a non cylindrical body portion such as the lower arm and wrist. The bandage 10 may be a rectangular plane structure as shown in FIG. 1 and rely on the adjustable tabs for proper fit, or may have a taper with different widths at the two ends and have a truncated triangular shape more suited to use on a tapering arm.

FIG. 6 is a front view of an embodiment to be used on a torso and shows the inner side non-stick surface 16 which will be in contact with the wound. There are two elastic leg openings 28 for placement of the patient's legs, and the bandage structure 10 has a shape designed to fit over the abdomen and part of the chest. The disclosed embodiment does not include an image of one or two adhesive strips for ease of understanding the figure, but one of ordinary skill may easily imagine the placement of a curved adhesive strip placed along the curved upper section of the bandage and disposed to assist the tabs 22 in securing the bandage as shown in FIG. 7.

FIG. 7 is a front view of FIG. 6 used on a torso and illustrates how the elastic cuffs 20 improve the leak resistance of the wound bandage garment 10 in the same fashion as discussed previously. The tabs 22 may be adhesive, or another attachment mechanism readily apparent to one of ordinary skill in the art, such as hook and loop fasteners, attached to appropriate pads on the outer side of the bandage portion located on the abdomen. In an embodiment the wound care bandage 10 covers enough of the chest to provide a fit to a body portion that does not taper in the downward direction, and thus provides a secure fit.

FIG. 8 is a side view of an embodiment to be used on a foot and demonstrates that the bandage 10 need not be a planar layer, but may have any three dimensional form required to provide a secure fit. This embodiment demonstrates that there do not need to be two cuffs 20 in all cases.

FIG. 9 is a side view of FIG. 8 used on a foot and shows how the tabs 22 may be used to adjust the fit to form a secure bandage. It should also be noted that in this embodiment the attachment strip 18 (not shown for simplicity), which may be adhesive, may be formed on either the inner or outer layer of the bandage.

CONCLUSION

The term "leak-proof" as used in the description may include material that substantially resists the movement of fluids such as water. Prepositions, such as "on", "side", "higher", "lower", "over" and "under", "top" and "bottom", "inner" and "outer" are defined with respect to the top of the bandage as laid out on a table, regardless of the orientation in use.

The detailed description refers to the accompanying drawings that show, by way of illustration, specific aspects and embodiments in which the present disclosed embodiments may be practiced. These embodiments are described in sufficient detail to enable those skilled in the art to practice aspects of the present invention. Other embodiments may be utilized, and changes may be made without departing from the scope of the disclosed embodiments. The various embodiments can be combined with one or more other embodiments to form new embodiments. The detailed description is, therefore, not to be taken in a limiting sense, and the scope of the present invention is defined only by the appended claims, with the full scope of equivalents to which they may be entitled. It will be appreciated by those of ordinary skill in the art that any arrangement that is calculated to achieve the same purpose may be substituted for the specific embodiments shown. This application is intended to cover any adaptations or variations of embodiments of the present invention. It is to be understood that the above description is intended to be illustrative, and not restrictive, and that the phraseology or terminology employed herein is for the purpose of description and not of limitation. Combinations of the above embodiments and other embodiments will be apparent to those of skill in the art upon studying the above description. The scope of the present disclosed embodiments includes any other applications in which embodiments of the above structures and fabrication methods are used. The scope of the embodiments should be determined with reference to the appended claims, along with the full scope of equivalents to which such claims are entitled.

What is claimed is:

1. An enclosing bandage for providing comfortable wound care and limiting fluid leakage, comprising:
- an inner layer, a middle layer, an outer layer, a top edge, a bottom edge, a right edge and a left edge, the inner layer being deformable and non-adherent,
- the outer layer being substantially impermeable to liquid, and being substantially coextensive with the inner layer,
- the middle layer being disposed between and contacting both the inner and outer layers, the middle layer being absorbent;
- at least one adjustable tab connected to at least one of the right edge and the left edge; and
- at least one cuff connected to the outer layer and disposed at a selected distance from at least one of the top edge and the bottom edge,
- wherein the bandage includes two substantially circular elastic holes positioned between the right and left edges and extending through the inner, middle and outer layers, said holes having a diameter adapted to enable insertion of a human leg into each hole.

* * * * *